(12) United States Patent
Sivan et al.

(10) Patent No.: US 8,563,297 B2
(45) Date of Patent: Oct. 22, 2013

(54) CONTROLLABLE BINDING AND DISSOCIATION OF CHEMICAL ENTITIES AND ELECTRODE DEVICES THEREFORE

(75) Inventors: Uri Sivan, Haifa (IL); Elad Brod, Tivon (IL)

(73) Assignee: Technion Research & Development Foundation Limited, Haifa (IL)

( * ) Notice: Subject to any disclaimer, the term of this patent is extended or adjusted under 35 U.S.C. 154(b) by 398 days.

(21) Appl. No.: 12/438,949

(22) PCT Filed: Aug. 30, 2007

(86) PCT No.: PCT/IL2007/001074
§ 371 (c)(1),
(2), (4) Date: Feb. 26, 2009

(87) PCT Pub. No.: WO2008/026214
PCT Pub. Date: Mar. 6, 2008

(65) Prior Publication Data
US 2009/0205974 A1    Aug. 20, 2009

Related U.S. Application Data

(60) Provisional application No. 60/841,212, filed on Aug. 31, 2006.

(51) Int. Cl.
*C12M 1/34* (2006.01)
*C12M 3/00* (2006.01)

(52) U.S. Cl.
USPC ...... 435/287.2; 435/283.1; 435/7.1; 436/518; 436/807

(58) Field of Classification Search
USPC .............. 435/287.2, 283.1, 7.1; 436/518, 807
See application file for complete search history.

(56) References Cited

U.S. PATENT DOCUMENTS

| | | | |
|---|---|---|---|
| 6,207,369 B1 * | 3/2001 | Wohlstadter et al. | 435/6 |
| 6,224,735 B1 * | 5/2001 | Akutsu et al. | 205/91 |
| 6,770,190 B1 | 8/2004 | Milanovski et al. | |
| 2002/0012943 A1 | 1/2002 | Fowlkes et al. | |
| 2003/0190632 A1 * | 10/2003 | Sosnowski et al. | 435/6 |
| 2008/0026408 A1 * | 1/2008 | Patton et al. | 435/7.5 |
| 2009/0069198 A1 * | 3/2009 | Havens et al. | 506/32 |
| 2009/0142789 A1 * | 6/2009 | Aastrup et al. | 435/29 |

FOREIGN PATENT DOCUMENTS

| | | |
|---|---|---|
| AU | 733305 | 5/2001 |
| WO | WO 2004/051274 | 6/2004 |
| WO | WO 2008/026214 | 3/2008 |

OTHER PUBLICATIONS

Response Dated Apr. 17, 2011 to Communication Pursuant to Article 94(3) EPC of Oct. 20, 2010 From the European Patent Office Re. Application No. 07805534.0.

(Continued)

*Primary Examiner* — Melanie Y Brown

(57) ABSTRACT

Disclosed are methods for controlling molecular interactions where at least one member of a pair of chemical entities having a pH-dependent affinity is immobilized on the surface of an electrode. By changing the potential difference between the electrode and a counter electrode, the affinity of the pair of chemical entities is changed, changing the tendency of the pair to bind or to dissociate. Disclosed are also devices useful for implementing the methods of the present invention.

24 Claims, 7 Drawing Sheets

(56) References Cited

OTHER PUBLICATIONS

Andreadis et al. "Use of Immobilized PCR Primers to Generate Covalently Immobilized DNAs for In Vitro Transcription/Translation Reactions", Nucleic Acids Research, 28(2): I-VIII, 2000.

Bergveld "Thirty Years of ISFETOLOGY. What Happened in the Past 30 Years and What May Happen in the Next 30 Years", Sensors and Actuators B, 88: 1-20, 2003.

Cabrera et al. "Formation of Natural pH Gradients in a Microfluidic Device Under Flow Conditions: Model and Experimental Validation", Analytical Chemistry, 73(3): 658-666, 2001.

Ghosh et al. "Transcription of T7 DNA Immobilised on Latex Beads and Langmuir-Blodgett Film", Journal of Biochemical and Biophysical Methods, 62: 51-62, 2005.

Klauke et al. "Characterisation of Spatial and Temporal Chenges in pH Gradients in Microfluidic Channels Using Optically Trapped Fluorescent Sensors", Lab on A Chip, 6: 788-793, 2006.

Orr "The Use of the 2-Iminobiotin-Avidin Interaction for the Selective Retrieval of Labeled Plasma Membrane Components", The Journal of Biological Chemistry, 256(2): 761-766, 1981. Abstract.

Communication Pursuant to Article 94(3) EPC Dated Oct. 20, 2010 From the European Patent Office Re. Application No. 07805534.0.

International Preliminary Report on Patentability Dated Mar. 12, 2009 From the International Bureau of WIPO Re. Application No. PCT/IL2007/001074.

International Search Report and the Written Opinion Dated Jan. 2, 2008 From the International Searching Authority Re. Application No. PCT/IL2007/001074.

Macounová et al. "Generation of Natural pH Gradients in Microfluidic Channels for Use in Isoelectric Focusing", Analytical Chemistry, 72(16): 3745-3751, 2000.

Communication Pursuant to Article 94(3) EPC Dated Feb. 6, 2012 From the European Patent Office Re. Application No. 07805534.0.

Communication Pursuant to Article 94(3) EPC Dated Aug. 6, 2013 From the European Patent Office Re. Application No. 07805534.0.

\* cited by examiner

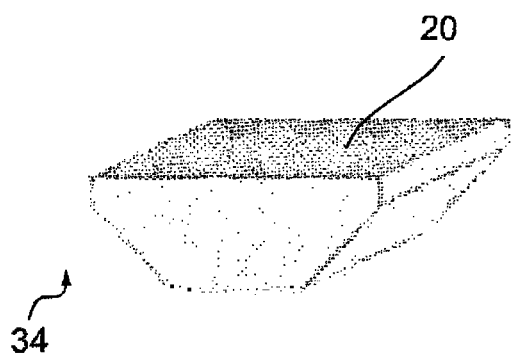
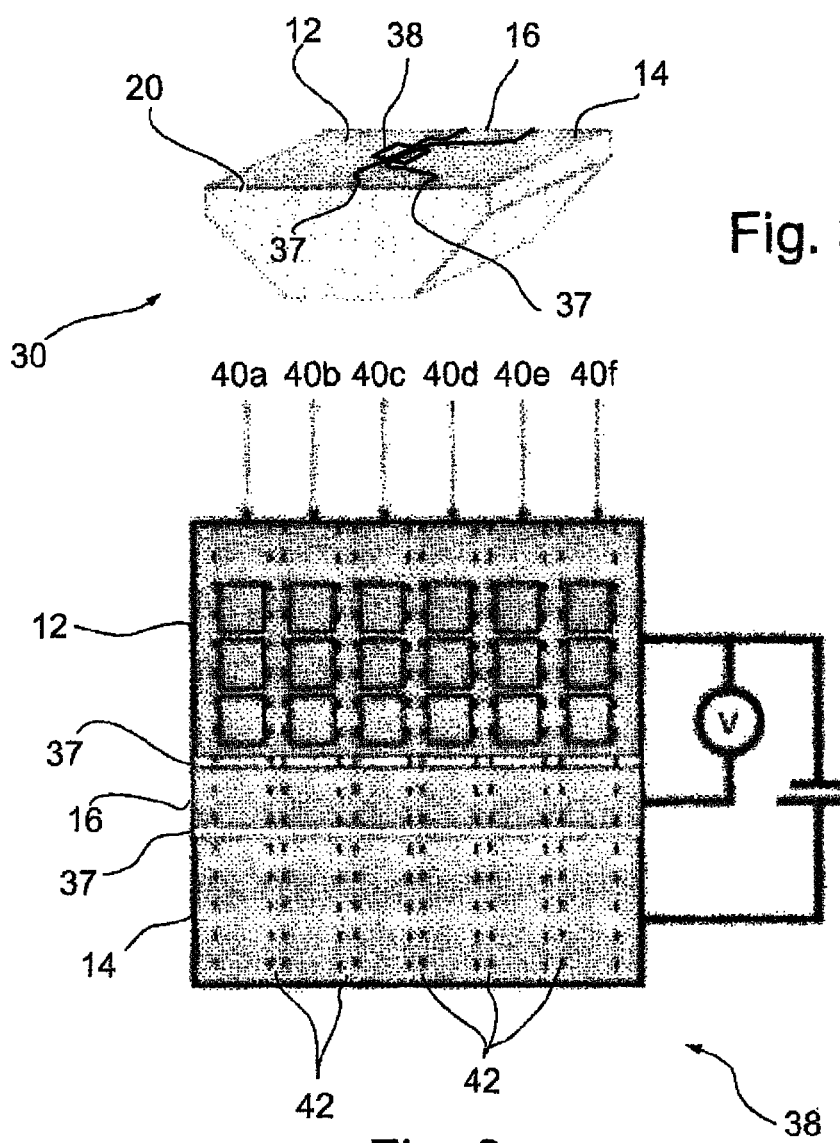
Fig. 3a
Fig. 3b
Fig. 3c

US 8,563,297 B2

CONTROLLABLE BINDING AND DISSOCIATION OF CHEMICAL ENTITIES AND ELECTRODE DEVICES THEREFORE

RELATED APPLICATIONS

This Application is a National Phase of PCT Patent Application No. PCT/IL2007/001074 having International filing date of Aug. 30, 2007, which claims the benefit of U.S. Provisional Patent Application No. 60/841,212 filed on Aug. 31, 2006. The contents of the above Applications are all incorporated herein by reference.

FIELD AND BACKGROUND OF THE INVENTION

The present invention relates to the field of molecular interactions, and particularly to methods and devices related to the controlled binding and dissociation of the members of a pair of chemical entities having a pH-dependent affinity.

An affinity pair is a pair of two molecules that mutually bind with high specificity. For many affinity pairs, mutual binding occurs through formation of multiple non-covalent bonds such as hydrogen bonds, electrostatic bonds, polarization interactions, Van der Waals forces and hydrophobic interactions. Although any one individual such non-covalent bond is relatively weak, the sum of the contributions of many such non-covalent bonds is such that the attraction (the affinity) between the two molecules making up the affinity pair is very strong. The high specificity of binding of affinity pairs is often a result of the fact that affinity is a function of the sum of many non-covalent interactions, the strength of which is for the most part highly geometry-dependent. For this reason, affinity pair association is often described using a "lock and key" or "puzzle piece" analogy.

The members of affinity pairs are known to belong to different and varied groups of molecules. One common type of affinity pair is an antibody/antigen pair.

An antibody is a protein produced by an organism that binds to an antigen, a molecule that is frequently, but not always, a peptide or protein. Antibody to antigen bonding is highly specific, so that a given antibody generally binds only to a specific antigen through a part of the antigen called an epitope.

As noted above, binding between the members of an affinity pair is through non-covalent bonds, including electrostatic attraction, polarization interactions and hydrogen bonds between protonable functional groups. Further, many types of molecules that are members of an affinity pair, such as peptides and proteins, have a conformation that is in a large measure determined by non-covalent interactions such as electrostatic interactions and internal hydrogen bonds between protonatable groups (e.g., secondary and/or tertiary structure). The degree of protonation of a molecule is in a large part determined by the availability of protons in the environment (most often an aqueous solution, but also others such as gels and the like) in which the molecule is found. In such cases, the affinity pair is characterized as having a pH-dependent affinity. The pH of the environment in which the affinity pair is found influences the degree to which the affinity pair is bound or dissociated by determining the affinity of the affinity pair by influencing the conformation of one or both of the members of the affinity pair and by influencing the degree of protonation of the functional groups through which the members of the affinity pair bind.

The pH dependence of the affinity of an affinity pair and consequence pH dependence on the degree of binding of an affinity pair has been used, for example, for affinity chromatography in the isolation of antibodies from a solution. A specific antigen is immobilized on a matrix to make a stationary phase. An eluent including the desired antibody, that together with the immobilized antigen constitutes an affinity pair, is passed along the stationary phase when the pH of the solution is such that the affinity of the affinity pair is high. Due to the high affinity and the high specificity of the affinity pair, only the antibody binds to the stationary phase. The stationary phase is washed with a washing phase having a pH where the affinity of the affinity pair is high, washing away undesired molecules while the antibody remains bound to the stationary phase. Subsequently, the bound antibodies are released from the stationary phase with an elution solution having a pH where the affinity of the affinity pair is low. The affinity pair dissociates and the antibody is isolated. A disadvantage of affinity chromatography is the requirement to provide and use different solutions having different pHs.

It would be useful to accurately control the degree of binding or dissociation of affinity pairs having a pH-dependent affinity without the use of different solutions having different pHs.

SUMMARY OF THE INVENTION

Some embodiments of the teachings of the present invention provide methods for influencing the binding and dissociation of pairs of chemical entities, such as affinity pairs, having a pH-dependent affinity in the proximity of an electrode. In some embodiments, the influence is reversible. Some embodiments of the teachings of the present invention provide devices that are useful for influencing the binding and dissociation of the members of a pair of chemical entities, such as an affinity pair, having a pH-dependent affinity.

According to the teachings of the present invention there is provided for a method of changing the affinity of a pair of chemical entities having a pH-dependent affinity, comprising: a) immobilizing a first member of a pair of chemical entities having a pH-dependent affinity to a surface of an electrode; b) immersing the first member of the pair of chemical entities in an electrolysable environment so that the electrode is in electrical contact with the environment where a second member of the pair of chemical entities is found in the environment; c) making electrical contact between a counter electrode and the environment; and d) changing a potential between the electrode and the counter electrode so as to substantially change electrolysis of the electrolysable environment thereby changing the affinity of the chemical entities by substantially changing a concentration of electrolysis products in the environment in proximity of the surface of the electrode. By changing electrolysis is meant, for example, the rate of electrolysis or the type of electrolysis reaction.

In some embodiments, the first member of the pair of chemical entities comprises amino acid residues. In some embodiments, the first member of the pair of chemical entities is a molecule selected from the group consisting of peptides, polypeptides and proteins.

In some embodiments, the second member of the pair of chemical entities comprises amino acid residues. In some embodiments, the second member of the pair of chemical entities is a molecule selected from the group consisting of peptides, polypeptides and proteins.

In some embodiments, the pair of chemical entities constitutes an affinity pair.

In some embodiments, the electrolysis products are products of electrolysis of water. In some embodiments, the electrolysis products comprise hydroxyl anions, in some embodiments the hydroxyl anions are products of an electrolytic reduction of water in the environment. In some embodiments, the electrolysis products comprise protons, in some embodiments the protons are products of an electrolytic oxidation of water in the environment.

In some embodiments, the changing of the concentration of electrolysis products is a lowering of the concentration of the electrolysis products.

In some embodiments, the changing of the concentration of electrolysis products is an increase of the concentration of the electrolysis products.

In some embodiments, the change of the affinity is an increase in affinity leading to increased binding of the second member to the first member of the pair of chemical entities, in some embodiments of the present invention useful for implementing affinity chromatography.

In some embodiments, the change of the affinity is a decrease in affinity leading to decreased binding of the second member to the first member of the pair, useful, for example, for dissociating bound pairs of the chemical entities.

In some embodiments, the change of concentration of the electrolysis products in the environment is substantial up to about 100 nanometer, up to about 30 nm, up to about 10 nm and even up to about 3 nm from the surface of the electrode.

In some embodiments of the present invention, the method further comprises: d) monitoring a pH of the environment in the proximity of the surface. In some embodiments, the changing of the potential between the electrode and the counter electrode to change the affinity of the pair of chemical entities is with reference to the monitoring, for example to achieve or maintain a desired pH in the proximity of the surface of the electrode.

In some embodiments, subsequent to the immobilizing, the first member of the affinity pair constitutes a monolayer on the surface of the electrode.

In some embodiments, the first member of the affinity pair is immobilized directly to the surface of the electrode.

In some embodiments, the environment comprises and even essentially consists of water. In some embodiments, the environment essentially consists of a gel, especially a hydrogel. In some embodiments, the environment is a fluid. In some embodiments, the environment comprises an aqueous solution.

In some embodiments, the environment is buffered. In some embodiments, the environment has a low buffering capacity. In embodiments, the buffering capacity $\beta$ is less than about 0.01 M, less than about 0.006 and even less than about 0.0033M, where $\beta=dn/d(pH)$ where n is number of equivalents of added strong base. In some embodiments, the concentrations of the buffer ingredients are at less than standard values. In some embodiments, the difference between the pH of the environment and the pKa of the buffer in the environment is greater than one pH unit ($|pH-pKa|>1$).

In some embodiments, the environment is an unbuffered environment.

In some embodiments, the surface of the electrode is configured for electrolysis of water, for example comprises or essentially consists of gold and/or platinum. In some embodiments the surface of the electrode is configured for reductive electrolysis of water to produce hydroxyl anions (usually accompanied with the production of $H_2$). In some embodiments the surface of the electrode is configured for oxidative electrolysis of water to produce protons (usually accompanied with the production of $O_2$).

In some embodiments, the electrode is configured to allow a flow of liquid therethrough. For example, in some embodiments, the electrode comprises multiple sheets, capillary channels, particulates or a porous material so as to have a high surface area relative to internal volume.

In some embodiments, the second member of the pair of chemical entities is substantially free to move in the environment and is not immobilized to the electrode. In some such embodiments, the potential between the electrode and the counter electrode is changed so that the affinity of the pair of chemical entities is high and the second member of the pair binds to the first member and is thus extracted from the environment. When desired, the potential is changed so that the affinity of the pair of chemical entities is low and the second member of the pair dissociates from the first member, releasing the second member to the environment.

Thus, according to some embodiments of the teachings of the present invention there is provided a method for extracting a member of a pair of chemical entities, for example a member of an affinity pair, from an environment. Some such embodiments of the present invention substantially constitute electrically controlled affinity chromatography where the stationary phase comprises the immobilized member of the pair of chemical entities. Thus according to the teachings of the present invention there is provided a method for performing affinity chromatography. In some such embodiments, the second member of the pair is extracted from an eluent (the environment) when the potential between the electrode and the counter electrode is changed so that the affinity of the pair is high. Subsequently, the extracted second member of the pair is eluted by changing the potential between the electrode and the counter electrode so that the affinity of the pair is low. As discussed hereinbelow, in some embodiments the pair is an affinity pair, in some embodiments an antibody/antigen affinity pair.

In some embodiments of the present invention, the pair of chemical entities is an antibody-antigen pair affinity pair. In some embodiments, the first member (immobilized to the electrode surface) is the antibody and the second member is the antigen. In some embodiments, the first member (immobilized to the electrode surface) is the antigen and the second member is the antibody. In some embodiments, the changing of the potential increases the affinity of the affinity pair so that the antibody binds to the antigen. In some embodiments, the changing of the potential decreases the affinity of the affinity pair so that bound antibody dissociates from the antigen.

In some embodiments of the present invention, the method further comprises: immobilizing the second member of the pair of chemical entities to the surface of the electrode so that the first member and the second member of the pair of chemical entities are within binding distance. In some embodiments, subsequent to the immobilizing, the second member of the affinity pair constitutes a monolayer on the surface of the electrode. In some embodiments, the second member of the affinity pair is immobilized directly to the surface of the electrode. In some embodiments, the second member of the pair is interspersed between the first member of the pair. In some embodiments, the changing of the potential between the electrode and the counter electrode increases the affinity of the pair of chemical entities so that the first member and the second member bind while attached to the surface of the electrode. In some embodiments, the changing of the potential decreases the affinity of the pair of chemical entities so that the first member and the second member, if bound, dissociate while attached to the surface of the electrode.

In some such embodiments, the teachings of the present invention are used to generate a switch or toggle having at least two states. In one state, the potential between the electrode and the counter electrode is such that the concentration of electrolysis products in proximity of the electrode surface is such that the affinity of the pair of chemical entities is high so that the chemical entities bind and are not exposed to interaction with other chemical entities, compounds or reagents in the environment. In another state, the potential between the electrode and the counter electrode is such that the concentration of electrolysis products in proximity of the electrode surface is such that the affinity of the pair of chemical entities is low so that the bound chemical entities dissociate from each other and are found in a state that allows interaction with other chemical entities, compounds and/or reagents in the environment.

For example, in some such embodiments, the pair of chemical entities is a DNA/histone affinity pair. In some embodiments, the changing of the potential regulates transcription of the DNA. In some embodiments, the RNA polymerase is provided in the environment so as to allow the transcription of the DNA.

Thus, according to the teachings of the present invention there is also provided a method of regulating DNA transcription. As discussed above, DNA and histone are both immobilized to the surface of an electrode, immersed in an environment including RNA polymerase and the potential between the electrode and the counter electrode changed so that the affinity of the DNA/histone affinity pair is high so that the DNA binds to the histone and is not available for transcription. When it is desired to transcribe the DNA, the potential between the electrode and the counter electrode is changed so that the affinity of the DNA/histone affinity pair is low to such an extent that the DNA dissociates from the histone and is available for transcription. When desired, the potential is again changed to increase the affinity of the DNA-histone affinity pair to the extent that the DNA binds to the histone, and the DNA is no longer available for transcription.

According to the teachings of the present invention there is also provided a device for changing the affinity of a pair of chemical entities having a pH-dependent affinity, comprising: a) an electrode including a conductive surface; and b) immobilized to the conductive surface of the electrode, molecules making up a first member of a pair of chemical entities having a pH-dependent affinity.

In some embodiments, the pair of chemical entities constitutes an affinity pair.

In some embodiments, the device further comprises a counter electrode, functionally associated with the electrode. In embodiments, the electrode and counter electrode are configured for hydrolysis (electrolysis of water).

In some embodiments, the device further comprises a reference electrode functionally associated with the electrode and the counter electrode.

In some embodiments, the device further comprises a power supply, configured to apply a potential difference between the electrode and the counter electrode. In embodiments, the potential difference is sufficient for causing hydrolysis (electrolysis of water).

In some embodiments, the molecules of the first member of the pair of chemical entities comprise amino acid residues, e.g., peptides, polypeptides, proteins.

In some embodiments, the surface essentially consists of a material suitable for reductive electrolysis of water, e.g., gold or platinum.

In some embodiments, the molecules of the first member of the pair of chemical entities constitute a monolayer on the surface of the electrode.

In some embodiments, the molecules of the first member of the pair of chemical entities are immobilized directly to the surface of the electrode.

In some embodiments, the device further comprises a pH sensor configured to monitor the proton concentration in proximity of the surface of the electrode. In some embodiments, the proximity is of no more than about 100 nm, no more than about 30 nm, no more than about 10 nm and even no more than about 3 nm from the surface. For example, in embodiments a pH sensor is an ISFET device integrated with the electrode that monitors the proton concentration at the surface of the electrode.

In some embodiments, the device further comprises a display unit, functionally associated with the pH sensor and configured to report a concentration of protons determined by the pH sensor. In some embodiments, the device further comprises a power supply controller, allowing a user to vary a potential between the electrode and the counter electrode so as to substantially maintain a desired proton concentration in the proximity of the surface of the electrode. For example, in some such embodiments, the user sees the proton concentration measured by the pH sensor displayed on the display unit and uses the power supply controller to change the potential between the electrode and the counter electrode, to change the affinity of the affinity pair.

In some embodiments of the present invention, the device further comprises a feedback controller configured to accept a value of proton concentration determined by the pH sensor and, based on the concentration, regulate a potential between the electrode and the counter electrode. In some embodiments, the feedback controller includes a user interface, allowing a user to input a desired proton concentration and the feedback controller controls the potential between the electrode and the counter electrode so as to substantially maintain the desired proton concentration in the proximity of the surface of the electrode.

In some embodiments, the device further comprises a container for maintaining the conductive surface of the electrode immersed in an electrolysable environment. In some embodiments, the device further comprises an electrolysable environment. In some embodiments, the environment comprises or even essentially consists of water. In some embodiments, the environment is a fluid. In some embodiments, the environment is a gel. In some embodiments, the environment is buffered. In some embodiments, the environment has a low buffering capacity. In embodiments, the buffering capacity β is less than about 0.01 M, less than about 0.006 and even less than about 0.0033M. In some embodiments, the concentrations of the buffer ingredients are at less than standard values. In some embodiments, the difference between the pH of the environment and the pKa of the buffer in the environment is greater than one pH unit (|pH−pKa|>1). In some embodiments, the environment is an unbuffered environment.

As noted above, the teachings of the present invention allow extraction of a member of an affinity pair from an environment. Thus, according to the teachings of some embodiments of the present invention there is also provided a device for extracting a member of a pair of chemical entities having a pH dependent affinity from an environment.

As noted above, the teachings of the present invention allow implementation of electrically controllable affinity chromatography. Thus, according to the teachings of some embodiments of the present invention there is also provided a device for performing electrically controllable affinity chromatography where the stationary phase comprises molecules of an immobilized member of a pair of chemical entities having a pH dependent affinity.

For example, in some embodiments, the molecules of the first member of the affinity pair are antigen molecules of an antibody-antigen affinity pair. In some embodiments, the molecules of the first member of the affinity pair are antibody molecules of an antibody-antigen affinity pair.

In some embodiments, the device further comprises a flow chamber including a fluid inlet and a fluid outlet, and wherein the electrode is located within the flow chamber so that fluid entering the flow chamber through the fluid inlet passes the surface of the electrode prior to exiting the flow chamber through the fluid outlet. In some embodiments, the fluid passes through the electrode, e.g., the electrode is porous, fibrous, particulate or comprises a bundle of capillary tubes. In some embodiments, the electrode comprises channels of a diameter less than about 10 micrometers and even less than about 5 micrometers, allowing a flow of liquid therethrough. In such a way, the electrode has a relatively high surface area compared to volume allowing more efficient interaction with an eluent and extraction of molecules of the second member of the pair of chemical entities, as is known to one skilled in the art of chromatography.

As noted above, in some embodiments the teachings of the present invention are applied to controlling the affinity of a pair of chemical entities where both members of the pair are immobilized on the surface of the electrode.

In some embodiments of the present invention, the device further comprises molecules of the second member of the pair of chemical entities immobilized to the conductive surface of the electrode. In some embodiments, the molecules of the second member of the pair of chemical entities constitute a monolayer on the surface. In some embodiments, the molecules of the second member of the pair of chemical entities are immobilized directly to the surface of the electrode. In some embodiments, the molecules of the second member of the pair of chemical entities and the molecules of the first member of the pair of chemical entities are within binding distance. In some embodiments, the molecules of the second member of the pair of chemical entities are interspersed between the molecules of the first member of the pair of chemical entities so as to be within binding distance.

In some embodiments of the present invention, the molecules of the second member of a pair of chemical entities comprise amino acid residues, e.g, are peptides, polypeptides, proteins.

As discussed above, in some such embodiments of the present invention, transcription of DNA is regulated. Thus, according to the teachings of some embodiments of the present invention there is also provided a device for regulating expression of DNA.

In some embodiments, the molecules of the first member of the pair of chemical entities are DNA molecules and the molecules of the second member of the pair of chemical entities are histone molecules.

In some embodiments, the molecules of the first member of the pair of chemical entities are histone molecules and the molecules of the second member of the pair of chemical entities are DNA molecules.

As noted above, according to embodiments of the teachings of the present invention there is also provided an affinity chromatography device for extracting a chemical entity from a fluid, comprising: a) an electrode including a conductive surface; b) immobilized to the conductive surface as a (chromatographic) stationary phase, molecules making up a first member of pair of chemical entities including the chemical entity to be extracted, the pair of chemical entities having a pH-dependent affinity; c) a counter electrode, functionally associated with the electrode; and d) a flow chamber including a fluid inlet and a fluid outlet, wherein the electrode is located within the flow chamber so that fluid entering the flow chamber through the fluid inlet passes the surface of the electrode prior to exiting the flow chamber through the fluid outlet. According to some embodiments, the molecules of the first member of the pair of chemical entities are antigen molecules of an antibody-antigen affinity pair. According to some embodiments, the molecules of the first member of the pair of chemical entities are antibody molecules of an antibody-antigen affinity pair. According to some embodiments, the electrode and the flow chamber are configured so that fluid entering the flow chamber through the fluid inlet passes through the electrode.

As noted above, according to embodiments of the teachings of the present invention there is also provided a device for regulating a chemical reaction, comprising: a) an electrode including a conductive surface; b) immobilized to the conductive surface, molecules making up a first member of a pair of chemical entities having a pH-dependent affinity; and c) immobilized to the conductive surface, molecules making up a second member of the pair of chemical entities; wherein the molecules making up a first member of the pair of chemical entities are interspersed between the molecules making up a second member of the pair of chemical entities so as to be within binding distance of the molecules making up a second member of the pair of chemical entities. According to some embodiments, the device further comprises a counter electrode, functionally associated with the electrode.

As noted above, according to embodiments of the teachings of the present invention there is also provided a device for regulating DNA transcription, comprising: a) an electrode including a conductive surface; and b) immobilized to the conductive surface, DNA molecules and histone molecules constituting an affinity pair having a pH-dependent affinity wherein the DNA molecules are interspersed between the histone molecules so as to be within binding distance of the histone molecules. According to some embodiments, the device further comprises a counter electrode, functionally associated with the electrode.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

As used herein, the indefinite articles "a" and "an" mean "at least one" or "one or more".

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of some embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 3A, 3B and 3C depict an electrode assembly on an SPR chip used to experimentally test the teachings of the present invention;

DESCRIPTION OF SOME EMBODIMENTS

Figure 1A:
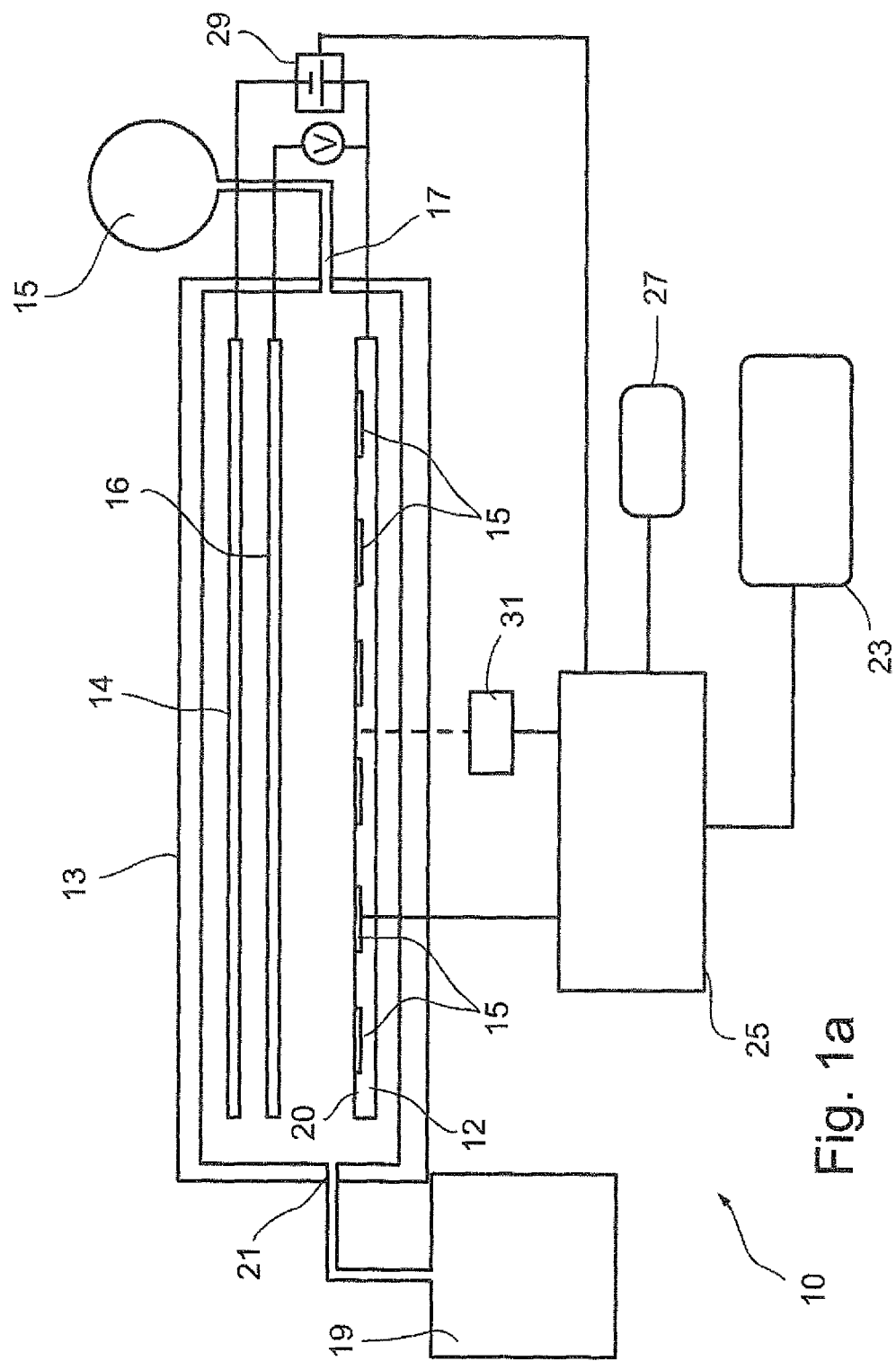
FIGS. 1A, 1B, 1C and 1D schematically depict an embodiment of the present invention for influencing the binding and dissociation of an antibody/antigen affinity pair having a pH-dependent affinity where an antigen is immobilized on an electrode allowing extraction of the antibody from the environment.

The present invention relates to methods and devices for controlling the binding and dissociation of the members of a pair of chemical entities having a pH-dependent affinity.

The teachings of the present invention relate to the interaction of two chemical entities which, under certain conditions have a tendency to bind one to the other, the tendency related to the affinity of the chemical entities, that is, an energetic measure of the binding strength between the chemical entities.

The teachings of the present invention relate to the interactions of a pair of chemical entities having a pH-dependent affinity, that is to say an affinity which value is influenced by the pH of the environment in which the respective two chemical entities are found. When the environment is at a first pH, the members of the pair have a tendency to bind and remain associated. When the environment is at a second pH, the members of the pair do not have a tendency, and if associated have a tendency to dissociate.

For example, pH-dependent affinity is known in the field of antibody-antigen affinity pairs, a property which is used when implementing affinity chromatography. Similarly, it is known that DNA-histone affinity pairs have a pH-dependent affinity.

Herein the term chemical entities generally relates to ions, atoms, and molecules, including small molecules, organic molecules, multifunctional molecules, polyfunctional molecules, organic acids, sugars and fatty acids. In some embodiments, the teachings of the present invention relate to an "affinity pair", a pair of two molecules that mutually bind with high specificity. Typical affinity pairs include pairs where one or both members of the affinity pair comprise amino-acid residues (e.g., peptides, polypeptides, proteins, for example antigen-antibody affinity pairs or DNA-histone affinity pairs).

According to the teachings of the present invention at least one member of a pair of chemical entities having a pH-dependent affinity is immobilized on the surface of an electrode and immersed in an electrolysable environment together with a counter electrode. In general, the electrode to which the chemical entity is immobilized is the working electrode, that is to say the electrode at which an electrochemical reaction, such as electrolysis, occurs. The potential between the electrode and the counter electrode is changed so as to substantially change electrolysis of the electrolysable environment (for example, the rate of electrolysis or the type of electrolysis reaction). As a result of the substantial change of electrolysis, there is a substantial change of the concentration of electrolysis products in the environment in the proximity of the electrode, which changes the affinity of the pair of chemical entities.

Thus, the teachings of the present invention provide for electrically controllable (by changing the potential difference between the electrode and the counter electrode) affinity of a pair of chemical entities. Such control is almost instantaneous and may be performed in real-time and continuously adjusted as required. By changing the affinity of the pair of chemical entities, the binding and dissociation of the pair is influenced and controlled. When the teachings of the present invention are applied to increase the affinity of a pair of chemical entities, the pair of chemical entities tends to bind. When the teachings of the present invention are applied to decrease the affinity of a pair of chemical entities, the pair of chemical entities tend to remain separate, and if already bound, to dissociate.

In some embodiments, the change of affinity is reversible. It has been found that the changing of the potential does not negatively affect the immobilized first chemical entity of a pair allowing an individual electrode to be used multiple times to bind and dissociate to the second chemical entity.

Any suitable electrolysable environment may be used in implementing the teachings of the present invention. By "electrolysable environment" is meant that there is at least one component in the environment that, under appropriate conditions, undergoes electrolysis to generate electrolysis products that influence the affinity of the pair of chemical entities. It has been found that, in some embodiments, the generation of affinity-changing electrolysis products is local (reaching substantial affinity-changing concentrations at a distance of no more than 100 nm, no more than 30 nm, no more than about 10 nm and even no more than about 3 nm from the electrode surface) and does not significantly affect the bulk of the environment.

Generally, the environment is an aqueous environment, comprising or even essentially consisting of water. In some embodiments, the environment is a gel, especially a hydrogel. In some embodiments, the environment is a fluid, for example an aqueous solution.

As is discussed herein, in some embodiments the electrolysis products that lead to the change of affinity of the pair of chemical entities are products of the electrolysis of water. In some embodiments, the electrolysis products comprise hydroxyl anions, in some embodiments the hydroxyl anions are products of an electrolytic reduction of water in the environment where water is reduced to hydroxyl anions and $H_2$ molecules. In some embodiments, the electrolysis products comprise protons, in some embodiments the protons are products of an electrolytic oxidation of water in the environment where the water is oxidized to protons and $O_2$ molecules.

It is important to note that in some embodiments of the present invention, the bulk characteristics of the environment (e.g., pH or composition) are not substantially changed. Rather, the affinity-changing electrolysis products are generated at the surface of the electrode and have a substantial affinity-changing concentration only close to the surface of the electrode, generally no more than about 100 nm, no more than about 30 nm, no more than about 10 nm and even no more than about 3 nm from the surface of the electrode. Further, in embodiments it is preferred that the interacting portion (e.g., epitope of an antigen) of the bonded member of the pair of chemical entities be within a distance from the surface of the electrode having a substantial affinity-changing concentration of the electrolysis products. Thus, in some embodiments, it is advantageous that any member (whether one or both) of a pair of chemical entities immobilized to the surface of the electrode be a monolayer and thus within the volume proximal to the electrode surface where an affinity-changing concentration of electrolysis products is present.

In some embodiments, the one or two chemical entities immobilized to the electrode surface are immobilized directly to the surface of the electrode. For example, in embodiments, the immobilized chemical entities include an immobilizing group to secure the chemical entity to the electrode surface, e.g., with the use of an amino acid linker sequence (e.g., CGGGS linker sequence, for example at a peptide N-terminus).

In some embodiments, the environment is buffered. It has been found that the buffering capacity of the environment has an influence on the distance from the electrode which the affinity-changing effect of the electrolysis products is substantial. Generally, in high-buffering capacity environments the distance is limited to very close (e.g., even less than 1 nm) to the electrode surface, which in embodiments may be too short of a distance to allow effective implementation of embodiments of the teachings of the present invention.

In some embodiments, it is preferred that the distance from the electrode surface where the electrolysis products have a substantial affinity-changing effect be greater than the distance in a high-buffering capacity buffer. Thus, in some embodiments, the environment has a low buffering capacity. In some embodiments, by low buffering capacity is meant that $\beta$ is less than about 0.01 M, less than about 0.006 and even less than about 0.0033M, where $\beta=dn/d(pH)$ where n is number of equivalents of added strong base. In some embodiments, by low buffering capacity is meant that the concentrations of the buffer ingredients are at less than standard values. In some embodiments by low buffering capacity is meant that the difference between the pH of the environment and the pKa of the buffer in the environment is greater than one pH unit ($|pH-pKa|>1$).

In some embodiments, the environment is an unbuffered environment.

In some embodiments, the change in potential between the electrode and the counter electrode is such that the affinity of the pair of chemical entities is increased, in some embodiments leading to controlled increase of the degree of binding of the members of the pair of chemical entities.

In some embodiments, the change in potential between the electrode and the counter electrode is such that the affinity of the pair of chemical entities is decreased, in some embodiments leading to controlled dissociation of bound members of the pair of chemical entities.

The teachings of the present invention provide for a variety of practical and useful methods and devices that can be implemented by one skilled in the art upon perusal of the description herein.

In some embodiments, only a first member of an affinity pair is immobilized on the surface of an electrode. By appropriately changing the potential between the electrode and the counter electrode, the degree of binding or dissociation of the immobilized first member of the pair of chemical entities with the second member of the pair of chemical entities in the environment is controlled.

In some such embodiments, the teachings of the present invention are used for affinity chromatography without needing an elution solution. Rather, the affinity of the pair of chemical entities is controlled by changing the potential between the electrode and the counter electrode so as to increase the affinity of the pair of chemical entities (to capture the second member from the environment) or decrease the affinity of the pair of chemical entities (to allow elution of the captured second member).

In some such embodiments, the teachings of the present invention are used for controlling the degree of attachment of a second member of an pair of chemical entities to an electrode surface.

In some such embodiments, the teachings of the present invention are used to determine the pH dependency of the affinity of spair of chemical entities, especially of an affinity pair.

In some embodiments, both the first and second member of a pair of chemical entities are immobilized on the surface of the same electrode in binding proximity one from the other. By appropriately changing the potential between the electrode and the counter electrode, the degree of binding or dissociation of the members of the pair of chemical entities is controlled.

In such an embodiment, a DNA-histone affinity pair is immobilized on the surface of an electrode. In a bound state, the DNA is bound to a nearby histone. When desired, the potential between the electrode and the counter electrode is changed so that the DNA dissociates from the histone and is susceptible to transcription by a transcription factor such as RNA polymerase in the solution.

Mechanisms

Although not wishing to be held to any one theory, it is hypothesized that, at least in some embodiments, the electrolysis products generated change the pH of the environment in the vicinity of the surface of the electrode. Since the affinity of the pairs of chemical entities is pH-dependent, the affinity is dependent on the concentration of electrolysis products in the proximity of the surface of the electrode. The concentration of electrolysis products is dependent, in part, on the potential between the electrode and the counter electrode, as the potential determines, in part, the rate of electrolysis.

In some embodiments, if the absolute value of the potential is increased there is more electrolysis and consequently a greater concentration of electrolysis products.

For example, in some embodiments, a negative potential applied to the electrode leads to reductive electrolysis of water to produce hydroxyl ions as affinity-changing electrolysis products and molecular hydrogen ($2H_2O+2e^- \rightarrow H_2 + 2OH^-$). In some such embodiments, increasing the absolute value of the applied potential increases electrolysis to produce more hydroxyl anions, raising the concentration of hydroxyl ions in proximity of the surface of the electrode. In some embodiments, produced hydroxyl anions react with protons in the environment, lowering the concentration of protons and therefore the pH in proximity of the electrode surface increases. A greater concentration of hydroxyl anions resulting from increased electrolysis raises the pH even further. Thus, all things being equal, in some embodiments more electrolysis leads to a higher concentration of hydroxyl anions and a higher pH, while less electrolysis leads to a lower concentration of hydroxyl anions and a lower pH in proximity of the surface of the electrode.

For example, in some embodiments, a positive potential applied to the electrode leads to oxidative electrolysis of water to produce protons as affinity-changing electrolysis products and molecular oxygen ($2H_2O \rightarrow O_2+4H^++4e^-$). In some such embodiments, increasing the absolute value of the applied potential increases electrolysis to produce more protons, raising the concentration of protons in proximity of the surface of the electrode and therefore lowering the pH in proximity of the electrode surface. A greater concentration of protons resulting from increased electrolysis lowers the pH even further. Thus, in some embodiments all things being equal, more electrolysis leads to a higher concentration of protons and a lower pH, while less electrolysis leads to a lower concentration of protons and a higher pH in proximity of the surface of the electrode.

Depending on the pH dependence of the pair of chemical entities, the change in the environment caused by the electrolysis may lead to an increase of affinity or a decrease of affinity. If the affinity increases, there is a greater tendency of the members of the pair to bind. If the affinity decreases, there is a greater tendency of bound members to dissociate and a lesser tendency of unbound members to bind.

In some embodiments of the present invention where the generated electrolysis products influence the concentration of protons in proximity of the electrode surface, it is advantageous to monitor the proton concentration with the help of a pH detector provided in proximity of the electrode surface. Monitoring of the proton concentration allows the potential between the electrode and the counter electrode to be changed, adjusted and controlled with reference to the proton concentration, allowing more accurate control and greater stability of the affinity of the pair of chemical entities.

A first embodiment of the present invention is discussed with reference to device 10 of the present invention schematically depicted in FIGS. 1A, 1B, 1C and 1D, device 10 substantially a device for implementing electrically controllable affinity chromatography in accordance with the teachings of the present invention. As discussed herein, device 10 is useful for extracting a member of an affinity pair (in device 10, an antibody) from an eluent.

Device 10 is schematically depicted in cross-section in FIG. 1A and comprises an electrode 12, a counter electrode 14 and a reference electrode 16 all contained within a flow chamber 13, which functions as a container for maintaining electrode 12 immersed in an electrolysable environment. Flow chamber 13 is functionally associated with pump 15 that forces an eluent into flow chamber 13 through a fluid inlet 17. Flow chamber 13 is also functionally associated with drain 19 through fluid outlet 21.

On the surface of electrode 12 are provided pH sensors 15 configured to monitor the concentration of protons in proximity of surface 20 of electrode 12. Typical pH sensors useful in implementing the teachings of the present invention are semiconductor devices that can detect protons concentration when immersed in solution, for example commercially available ion sensitive field-effect transistors (ISFET). In ISFET devices, conductivity is controlled by the potential imposed on an oxide gate exposed to the environment and presents available binding sites for protons. Binding of protons to the binding sites on the oxide gate results in a change of potential which, in turn, changes the conductivity of the device. The gating of this transistor is therefore dependent on the proton concentration in the environment. Such devices have been described, for example, in Bergveld, P. *Sensors and Actuators B*, 2003, 88, 1-20. The pH sensors are functionally associated with display unit 23 through controller 25 (e.g., comprising a general purpose computer). Controller 25 is configured to accept the values of proton concentration in proximity of surface 20 determined by pH sensors 15 and report the concentration on display unit 23.

Controller 25 is also functionally associated with power supply 29, allowing controller 25, autonomously, automatically or as a result of a user instruction received through input device 27 to change a potential difference between electrode 12 and counter electrode 14. Thus, controller 25 is configured to function as a power supply controller.

Controller 25 is also functionally associated with input device 27 so as to receive instructions from a user, for example, to activate or deactivate power supply 29.

Functionally associated with controller 25 is also a binding monitor 31, e.g. a Surface Plasmon Resonance (SPR) instrument. Binding monitor 31 measures the degree of analyte binding to surface 20 of electrode 12 and reports the result to controller 25.

Figure 1B:
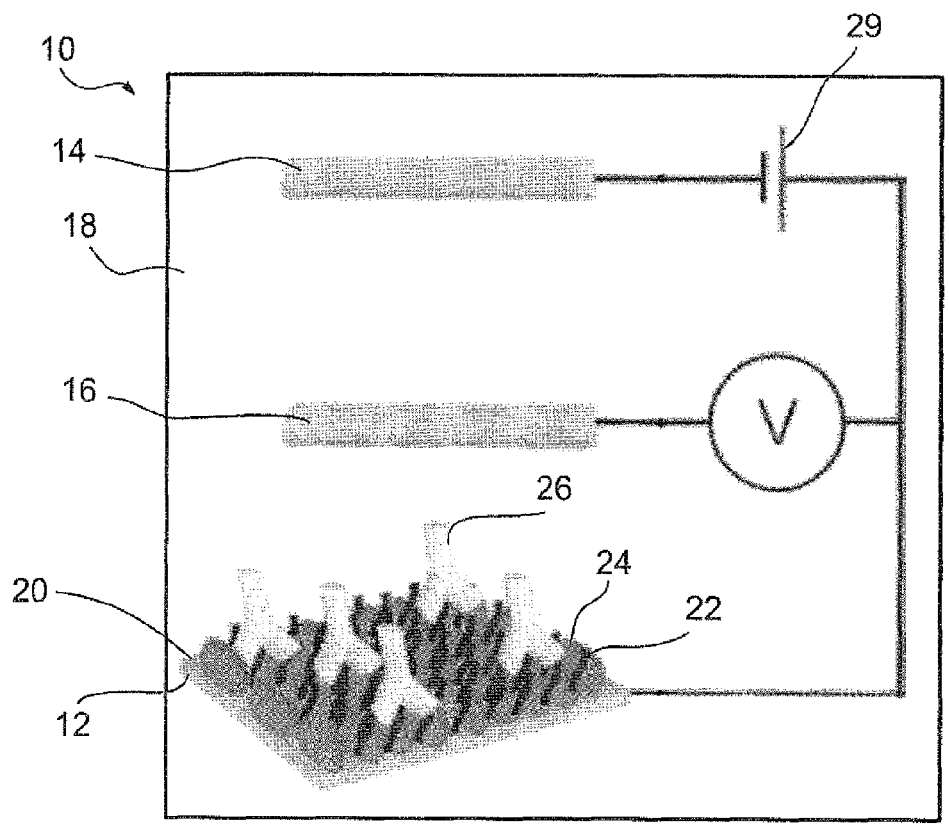
Figure 1C:
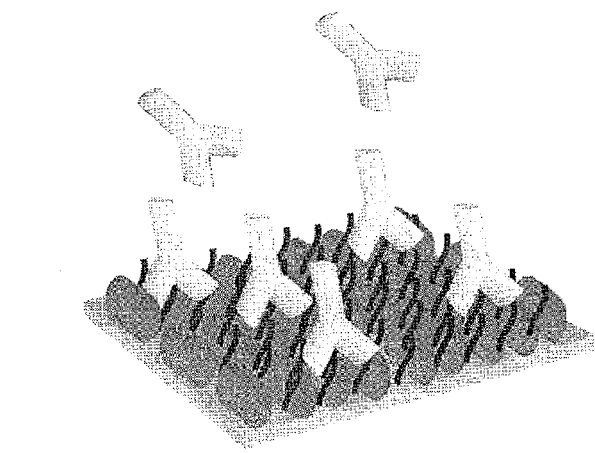

In FIG. 1B, surface 20 of electrode 12 is shown in detail. Surface 20 is conductive and comprises a layer of a material suitable for reductive electrolysis of water, e.g., gold or platinum. Immobilized to surface 20 is a monolayer of antigen molecules 22 (as molecules making up a first member of an affinity pair having a pH-dependent affinity) interspersed between a layer of bovine serum albumin 24 to prevent binding of other materials to surface 20.

An aqueous solution including an antibody 26 that, together with antigen 22, makes up an affinity pair is brought to a pH with the use of a buffer (e.g., PBS) as an eluent such that the affinity of the affinity pair is relatively high.

Pump 15 is activated, forcing the eluent into flow chamber 13 through fluid inlet 17 and past surface 20 of electrode 12. Due to the pH of the eluent, molecules of antibody 26 bind to molecules of antigen 22 (as depicted in FIG. 1B), while other materials are forced out through drain 19 through fluid outlet 21.

Eluent is replaced with a washing solution having a pH such that the affinity of the affinity pair is high and forced past outlet 21 to wash away undesired materials.

Figure 1D:
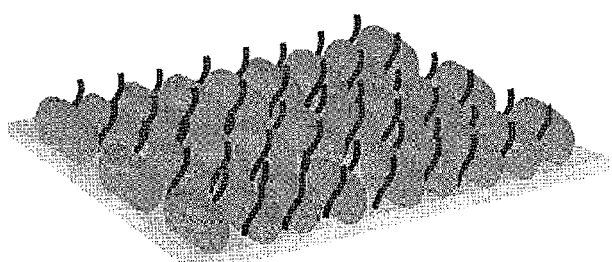

When the washing is sufficient, a user uses input device 27 to activate controller 25 to set power supply 29 to change the potential between electrode 12 and counter electrode 14 to a previously determined new potential value difference. At the new potential, electrolysis of water generates electrolysis products such as hydroxyl anions in proximity of surface 20 of electrode 12. The hydroxyl anions lower the affinity of antigen 22/antibody 26 affinity pairs. As a result of the lowered affinity, the affinity pairs dissociate (FIG. 1C), so that antibody molecules 26 are released into the environments and forced out through fluid outlet 21 to be isolated while antigen molecules 22 remain immobilized to surface 20 (FIG. 1D).

After antibody molecules 26 are released, the potential between electrode 12 and counter electrode 14 is changed to a potential where electrolysis does not occur and no electrolysis products are generated. As a result, the affinity of antigen 22 antibody 26 affinity pairs returns to a high value. A new batch of antibody 26/containing eluent may be introduced into flow chamber 13 and electrode 12 used again to extract antibody molecules 26 from the eluent.

In the embodiment discussed above, the potential between the electrode and counter electrode was changed a first time to increase the concentration of electrolysis products in the vicinity of surface 20 of electrode 12, an increased concentration that lowered the affinity of the affinity pair. Due to the low affinity, antibodies 26 in the eluent pass by antigens 22 and did not bind thereto. Bound antibodies 26 dissociated from antigens 22 and entered the eluent.

In the embodiment discussed above, the potential between the electrode and counter electrode was changed a second time to lower the concentration of electrolysis products in the vicinity of surface 20 of electrode 12, a lower concentration that increased the affinity of the affinity pair. Due to high affinity, antibodies 26 in the eluent have a tendency to bind to antigens 22 and are thus extracted from the eluent.

In the embodiment discussed above, antigens 22 are immobilized on surface 20 and are useful for extracting antibodies 26 from the eluent. In some embodiments, antibodies are immobilized on surface 20 and are useful for extracting antigens 22 from an eluent.

In the embodiment discussed above, surface 20 of electrode 12 is substantially planar and eluent flows past surface 20. In some embodiments, electrode 12 is configured to allow a flow of eluent therethrough, for instance is in the form of a crumpled/folded filament, multiple sheets, capillary channels, particulates or porous material. In some embodiments, the electrode comprises channels of a diameter less than about 10 micrometers and even less than about 5 micrometers, allowing a flow of liquid therethrough. In such some embodiments, the electrode is configured to have a high surface area to internal volume (as is known in the art of chromatography) to increase the density of the stationary phase (i.e., the number of antigen molecules 22 per unit volume) and to increase the probability that an analyte (i.e., an antibody molecule 26) will pass in proximity of surface 12 to interact with the stationary phase and be extracted from the eluent.

In the embodiment discussed above, the control of the potential between electrode 12 and counter electrode 14 was simple and controlled by the user who instructed controller 25 to change the potential using input device 27. If desired, the user can ascertain the concentration of protons in the vicinity of surface 20 as measured by pH sensors 15 to controller 25 and displayed on display unit 23.

In some embodiments, controller 25 accurately maintains the proton concentration in the vicinity of surface 20 of electrode 12 with reference to the proton concentration determined by pH sensors 15. A user inputs a desired pH to controller 25 using input device 27. Controller 25 continuously receives a value of proton concentration determined by pH sensors 15, and based on the value of the proton concentration, regulates the potential between electrode 12 and counter electrode 14 to adjust the generation of electrolysis products and consequently the pH in the vicinity of surface 20 of electrode 21. In such a way, a desired proton concentration is substantially maintained in the proximity of surface 20 of the electrode 12.

A second embodiment of the present invention is discussed with reference to device 27 of the present invention schematically depicted in FIGS. 2A and 2B, device 27 substantially a device for implementing electrically controllable DNA transcription in accordance with the teachings of the present invention. Device 27 is thus configured to regulate expression of DNA.

Device 27 comprises an electrode 12 on which gold surface 20 are immobilized two members of an affinity pair, histone H1 molecules 22 and DNA molecules 26. Both the histone molecules 22 and DNA molecules 26 are immobilized so as to constitute a monolayer of histone molecules 22 interspersed with a monolayer of DNA molecules 26 so that all DNA molecules 26 are within binding distance of enough histones so as to prevent transcription. In some embodiments, each DNA molecule 26 is within binding distance of at least one histone molecule 22, at least two histone molecules 22 and even at least five histone molecules.

Device 27 has substantially two states. In a first state, schematically depicted in FIG. 2A, the pH of the environment above surface 20 of electrode 12 is relatively low (e.g., pH≈7), so that the affinity of the DNA 26-histone 22 affinity pair is relatively high whereby DNA molecules 26 are condensed and wrapped around histone molecules 22, therefore unavailable for transcription. In a second state, schematically depicted in FIG. 2B, a potential between electrode 12 and a respective counter electrode is such that the affinity of the DNA 26-histone 22 affinity pair is relatively low whereby DNA molecules 26 are loose and available for transcription.

In accordance with the teachings of the present invention, switching or toggling between the first state and the second state is performed by changing the potential between electrode 12 and the respective counter electrode. A solution including a transcription factor 33 such as an appropriate RNA transcriptase is placed in proximity of surface 20 of electrode 12 when the pH of the solution is such that the affinity of the DNA 26-histone 22 affinity pair is relatively high, FIG. 2A.

Figures 2A, 2B:
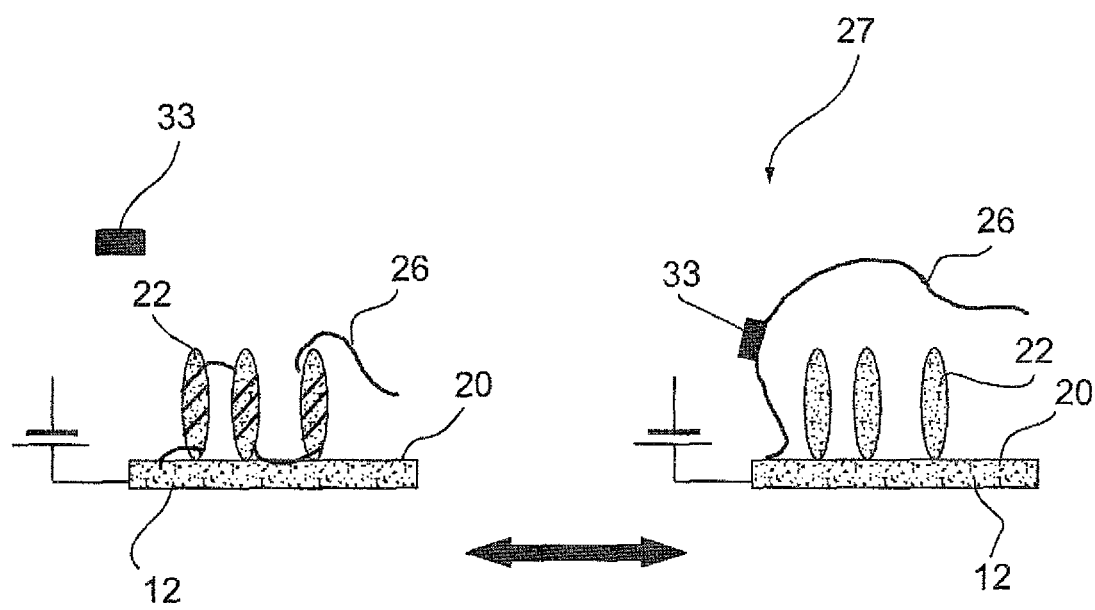
FIGS. 2A and 2B depict an embodiment of the present invention of a histone-DNA affinity pair where both members of the affinity pair are immobilized on an electrode allowing regulation of the transcription of the DNA.

When it is desired to transcribe the DNA, the potential between electrode 12 and the respective counter electrode is changed, for example to—1 V, leading to electrolysis (e.g., of water) to generate a relatively high concentration of electrolysis products (e.g., hydroxyl anions) in the vicinity of surface 20 of electrode 12 that lowers the affinity of the DNA 26-histone 22 affinity pair so that the DNA molecules 26 dissociate from histone molecules 22 and are available for transcription by transcription factor 33, FIG. 2B. Transcription is then performed in the usual way, see for example, Andreadis, J. D. and Chrisey, L. A. *Nucleic Acids Research* 2000, 28(2), e5, i-viii and Ghosh, D. et al. J. Biochem. Biophys. Methods 2005, 62, 51-62.

When it is desired to stop the DNA transcription, the potential between electrode 12 and the respective counter electrode is changed, for example to 0. Electrolysis stops, the concentration of electrolysis products decreases to a level where the affinity of the DNA 26-histone 22 affinity pair is relatively high, and DNA molecules 26 again becomes unavailable for transcription, FIG. 2A.

Additional objects, advantages, and novel features of the present invention will become apparent to one ordinarily skilled in the art upon perusal of the following non-limiting experiments.

Experimental

The teachings of the present invention were experimentally demonstrated by studying the controlled binding and dissociation of antibody/antigen affinity pairs having a pH-dependent affinity with the help of an electrochemical Surface Plasmon Resonance (SPR) instrument (ProteOn® XP SPR, Bio-Rad Inc., Haifa, Israel).

An electrode assembly 30 as depicted in FIGS. 3A, 3B and 3C was produced from a commercially available glass SPR chip delivered with the SPR instrument. The original chip (FIG. 3A, perspective) consists of a glass prism 34 on which 22 mm×22 mm top surface 20 two continuous polycrystalline layers are applied by vapor deposition. The first layer is a 10 nm thick chromium layer on the glass surface and the second layer is a 50 nm thick gold layer deposited on the chromium layer.

To study the teachings of the present invention, the continuous layer on top surface 20 was divided into three electrically separate layers electrode 12, counter electrode 14 and reference electrode 16, see FIG. 3B. To this end, two slits 37 spaced 1 mm apart were formed through the metal layers, by application of a gold etching solution followed by a chrome etching solution and extended to the edges of top surface 20 with a scriber.

The area between slits 37 was modified into an Ag/AgCl reference electrode 16. This was done by silver electroplating followed by electrolytic oxidation. The electroplating was performed by exposing the center (indicated with square 38 in FIG. 3B) of reference electrode 16 to an $AgNO_3$ solution and applying −10 mA with respect to a platinum electrode for 20 seconds. The oxidation of the plated silver layer was accomplished by immersing chip 34 in an HCl solution and applying 20V with respect to a platinum electrode for 30 seconds. The result was electrode assembly 30 consisting of three mutually electrically insulated electrodes 12, 14 and 16 as depicted in FIGS. 3B (perspective) and 3C (top view of square 38).

Area 38 of electrode assembly 30 studied in the experiments is depicted from above in FIG. 3C.

Antigens as a first member of an antibody/antigen affinity pair were immobilized to surface 20 of electrode 12, see below.

As with prior art SPR instruments, six parallel fluid channels (40a-40f) were defined on surface 20 of electrode assembly 30 by tightly securing a six channel RTV casting to electrode assembly 30 so that each channel was 450 micrometers, 100 micrometers wide, and was provided with a fluid inlet (fed with a 160 micrometer hose), a fluid outlet (drained with a 10 micrometer hose) and an independent flow control. The walls of the RTV castings made contact with upper surface 20 at dashed lines 42 indicated in FIG. 5C. Each channel 40 included an upstream part including a portion of electrode 12, a portion of reference electrode 16, and a downstream part including a portion of counter electrode 14.

Experiments generally included passing solutions of interest through channels 40 while monitoring the degree of antibody binding to antigens immobilized on electrode 12. To this end in each channel 40, three 400×400 micrometer square areas of interest (upstream, middle and downstream, see FIG. 3C) were monitored using the electrochemical Surface Plasmon Resonance (SPR) instrument.

All potentials were measured with reference to reference electrode 16. Electrical measurements were performed using a Parstat™ 2273 from Princeton Applied Research, Oak Ridge, Tenn., USA.

All solutions and buffers were prepared using doubly distilled water (18 MΩ) and analytical grade chemicals. Unless otherwise noted, the concentration of antibody in the antibody solutions was 48 microgram/ml. All antigens, antibodies, materials, solutions, reagents, buffers and other materials were purchased from Sigma-Aldrich, Co., St Louis Mo., USA.

Results

Two different antibody-antigen affinity pairs were studied.

The first affinity pair tested was monoclonal anti-Histone Deacetylase I (HDAC1) antibody with the peptide CGGGSKEEKPEAKGVKEEVKLA as an antigen.

The second affinity pair tested was monoclonal anti-Histone Deacetylase 3 (HDAC3) antibody with the peptide CGGGSNEFYDGDHDNDKESDVEI as an antigen.

For preparation of an experiment, an antigen was immobilized to a gold surface 20 of an electrode 12 of an electrode assembly 32 through the CGGGS linker sequence at the peptide N-terminus through the thiol side chain of the terminal Cystein residue to form a monolayer. Immobilization was performed by incubating an electrode 12 in a 1.1 microgram/ml antigen solution in a phosphate buffer solution (PBS) having a pH of 7.2 (137 mM NaCl, 2.7 mM KCl, 4.3 $Na_2HPO_4$, 1.4 mM $KH_2PO_4$). The thus-formed monolayers were measured using the SPR instrument and found to have a surface concentration on the order of $10^{13}$ antigen molecules/$cm^2$. Possible open spaces on electrode surface 20 were blocked with the use of a blocking solution of bovine serum albumin (5 mg/ml) which was injected into channels 40 in the usual way to prevent unspecific bonding of antibody to surface 20 of electrode 12.

Both of the antibody/antigen affinity pairs were studied in substantially the same way, yielding substantially similar results. For convenience and brevity, only the results of the affinity pair including the HDAC1 antibody are shown.

Association and Dissociation of Antibodies from an Antibody Solution

A continuous flow of an antibody solution was maintained in channel 40a with a concurrent continuous flow of a solution having the same pH devoid of antibody was maintained in reference channel 40b past electrode 12 while the potential applied to electrode 12 was varied. The amount of antibody bound to the antigen molecules immobilized on the surface of electrode 12 was monitored with the SPR instrument at each of the three areas of interest.

Figure 4:
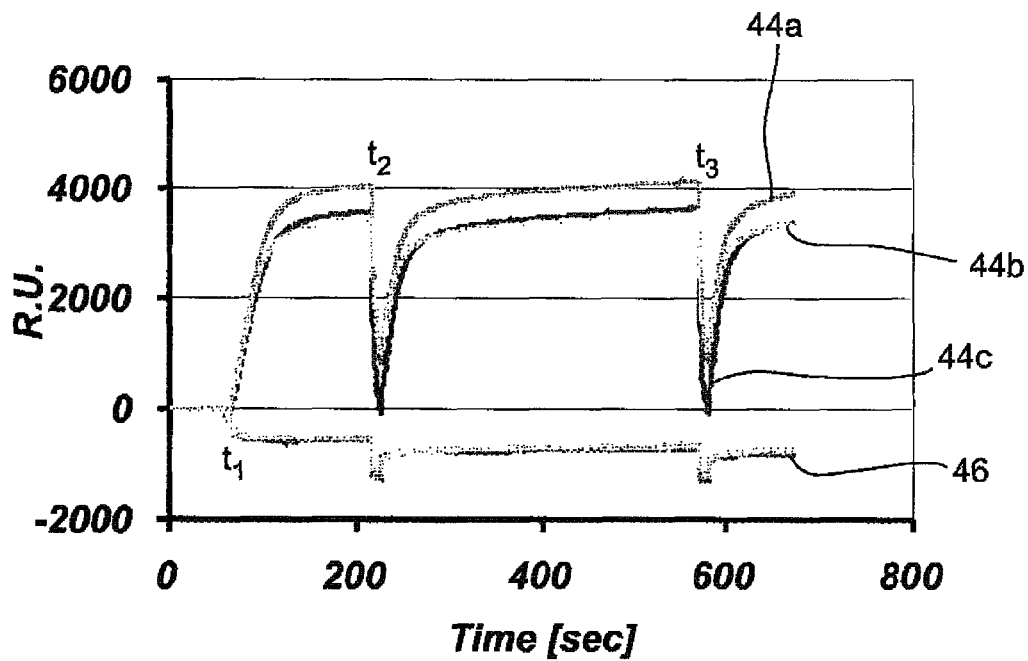
FIG. 4 shows experimental results demonstrating the controlled binding and dissociation of an antibody to an antigen immobilized on an electrode in accordance with the teachings of the present invention.

In FIG. 4 are depicted results (44a, 44b and 44c) showing the controlled binding and dissociation of an affinity pair in accordance with the teachings of the present invention, specifically the amount of antibody HDAC1 bound to an area of interest in channel 40a as a function of time. Results 46 show the SPR measurement in an area of interest in reference channel 40b.

At t0=0 seconds, a PBS solution (pH 7.2) was passed through channels 40a and 40b.

At t1=60 seconds, an HDAC1 antibody solution in PBS having a pH of 8.9 (137 mM NaCl, 2.7 mM KCl, 2.1 $Na_2HPO_4$, 0.7 mM $KH_2PO_4$) was passed through channel 40a so that HDAC1 antibody molecules from the solution bound to the immobilized antigen molecules. Simultaneously, PBS solution (pH 8.9) devoid of antibody was passed through reference channel 40b.

At t2=200 seconds when the antigen in channel 40a was saturated with antibody from the solution, a potential of −0.9V was applied to electrode 12 for 10 seconds. As is seen in FIG. 4, the bound antibody dissociated from the antigen substantially immediately. Presumably, products of electrolysis of the water (reduction to produce hydroxyl anions and $H_2$) lowered the affinity of the affinity pair, consequently leading to the dissociation of the antibody from the antigen. It is presumed that the hydroxyl anion electrolysis products reacted with protons in the solution in proximity of the surface of electrode 12, increasing the pH near the surface of electrode 12. Amongst other effects, it is presumed that positively charged amino acid residues, e.g., Lysine of the antigen or the antibody, were deprotonated by the hydroxyl anions lowering the affinity of the affinity pair and causing the bound affinity pairs to dissociate.

After the potential on electrode 12 returned to 0 V, antibody molecules from the solution again bonded to the immobilized antigen molecules. It is important to note that this result indicates that the monolayer of immobilized antigen molecules was not damaged or otherwise adversely affected and that the effects of applying a potential between the electrodes were reversible.

At t3=400 seconds when the antigen in channel 40a was saturated with antibody from the solution, a potential of −0.9V was again applied to electrode 12 for 10 seconds, again causing the bonded affinity pairs to dissociate.

After the potential on electrode 12 returned to 0 V, antibody molecules from the solution again bonded to the immobilized antigen molecules.

It is seen that the lowering of affinity of the affinity pairs caused by application of a reductive potential was reversible with no apparent effect such as desorption or loss of activity on the immobilized antigen monolayer.

It was observed that the degree of dissociation of the bound affinity pairs resulting from the applied potential was strongest for the area of interest closest to counter electrode 14 (compare 44a, 44b and 44c in FIG. 4), presumably due to ohmic losses along channel 40a.

The variations in the SPR results 46 of reference channel 40b was attributed to desorption of adsorbed ions (e.g., chlorine), charge accumulation in the gold electrode and minor desorption of the blocking proteins (BSA).

A similar experiment (results not shown) performed where each potential pulse was 40 seconds long showed that as long as potential was applied, no affinity pair binding occurred, demonstrating that the effect of applied potential (e.g., electrolysis of water, lowered affinity pair affinity) was persistent and not transient.

A similar experiment (results not shown) performed where the applied potential was positive did not cause dissociation of the affinity pair.

A similar experiment (results not shown) performed with an antibody that did not match the antigen immobilized on electrode 12 showed only negligible binding of antibody to the antigen.

Dissociation of Antibodies Bound to an Antigen

Antibody-antigen affinity pairs were bound on the surface of electrode 12 and dissociated, releasing the antibody into an antibody-free solution by the application of a potential to electrode 12. The amount of antibody bound to the antigen immobilized on surface 20 of electrode 12 was measured with the SPR instrument.

Figure 5:
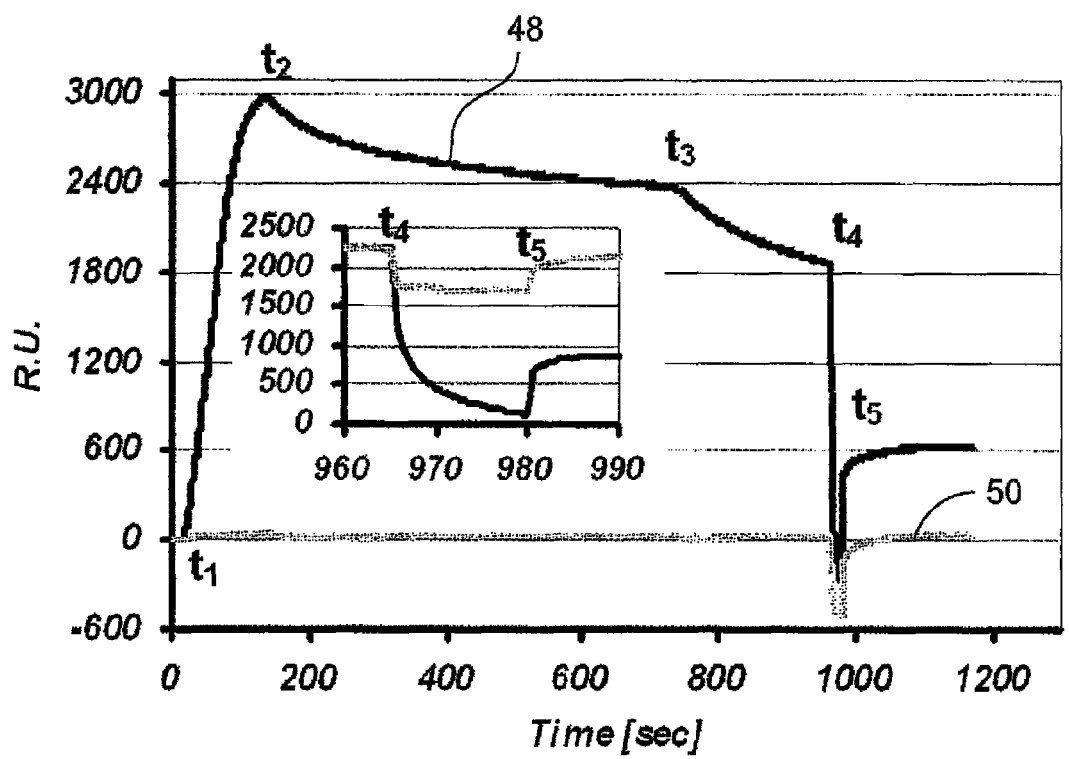
FIG. 5 shows experimental results demonstrating the controlled dissociation of an antibody to an antigen immobilized on an electrode in accordance with the teachings of the present invention.

In FIG. 5 are depicted results 48 showing the controlled dissociation of a bonded affinity pair in accordance with the teachings of the present invention, specifically the amount of antibody HDAC1 bonded to an area of interest in channel 40a as a function of time. Results 50 show the SPR measurement in an area of interest in reference channel 40b.

At t0=0 a PBS solution (pH 7.2) was passed through channels 40a and 40b.

At t1=10 seconds, an HDAC1 antibody solution in PBS (pH 7.2) was passed through channel 40a so that HDAC1 antibody molecules from the solution bonded with immobilized antigen molecules. Simultaneously, PBS solution (pH 7.2) devoid of antibody was passed through reference channel 40b.

At t2=160 seconds, a PBS solution (pH 7.2) devoid of antibody was passed through channel 40a. It is seen from result 48 that a minor proportion of affinity pairs slowly dissociated, releasing antibody molecules into the solution.

At t3=750 seconds, a PBS solution (pH 9.0) devoid of antibody was passed through channel 40a and reference channel 40b.

At t4=980 seconds, a potential of −0.9V was applied to electrode 12 for 15 seconds until t5=995 seconds. As discussed above, the applied potential lead to dissociation of the affinity pair and release of antibody molecules into the solution.

From the inset of FIG. 5 is seen that signal 48 in the antibody channel 40a resulted from two effects: a fast, fully reversible reaction of the PBS buffer solution with electrode surface 20 and the slower dissociation of the affinity pair.

Best exponential fits to time segments t2 to t3 (pH 7.2), t3 to t4 (pH 9.0) and t4 to t5 (pH 9.0) with controlled affinity pair dissociation according to the present invention) yielded 250±70, 150±20 and 4.5±1.0 seconds dissociation times, respectively. Thus, the controlled dissociation of affinity pairs in accordance with the teachings of the present invention increased the rate of dissociation more than 30 fold over the dissociation rate attributable to the pH of the solution.

Effect of Environmental Proton Concentration

Figure 6A:
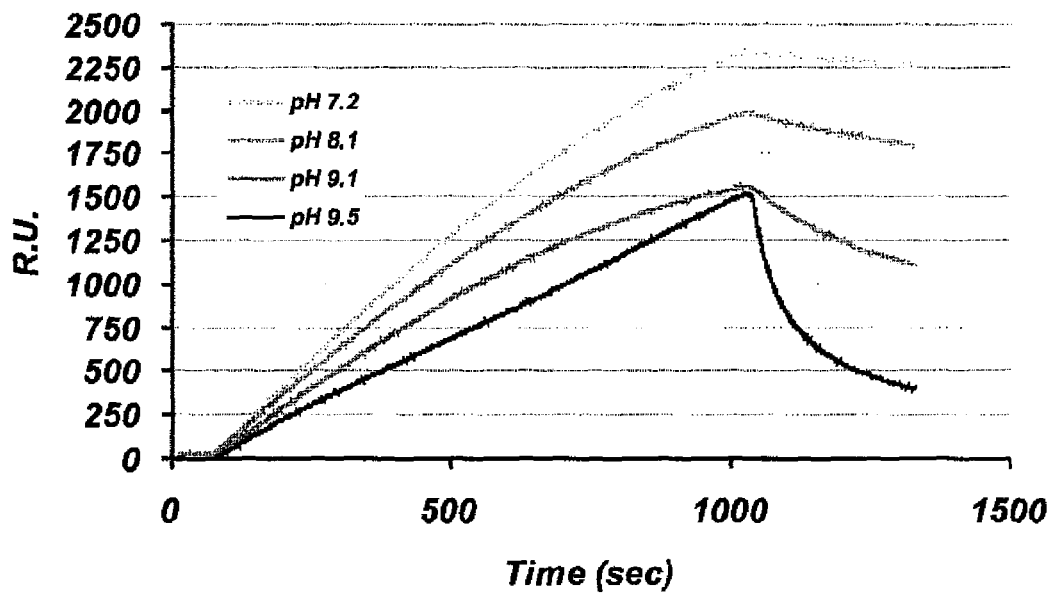
FIGS. 6A and 6B show experimental results demonstrating the effect of environmental pH on antibody binding (FIG. 6A) and on the controlled dissociation of an antibody to an antigen immobilized on an electrode in accordance with the teachings of the present invention.
Figure 6B:
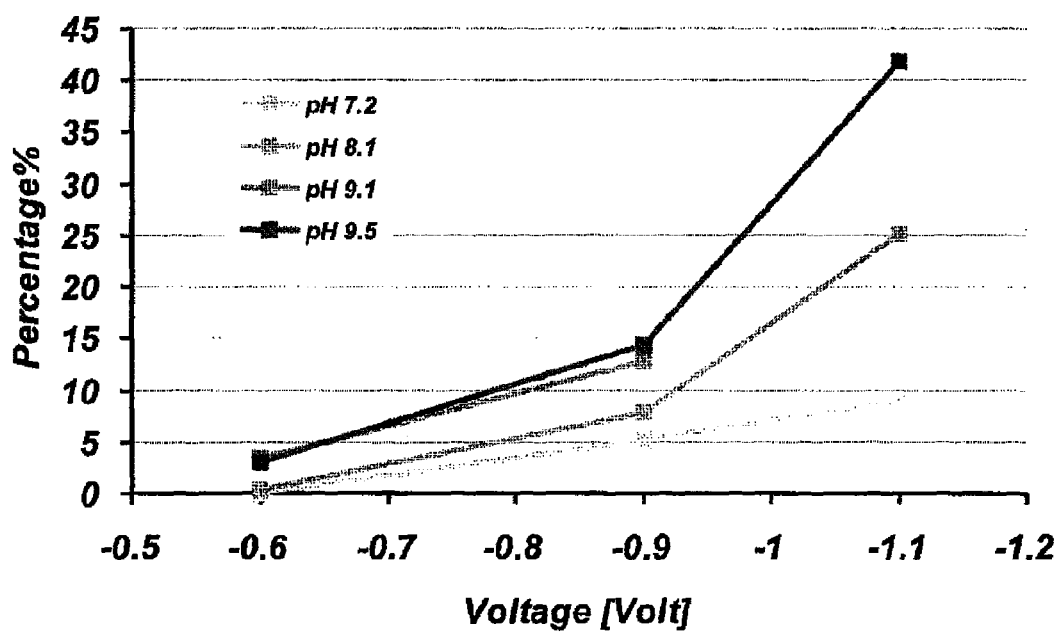

Results of a study of the effect of the pH of the solution are depicted in FIGS. 6A and 6B.

PBS buffered solutions including antibody, each solution having a different pH, were passed through four channels 40a (pH 7.2), 40b (pH 8.1), 40c (pH 9.1) and 40d (pH 9.5). As is seen from FIG. 6A, antibody molecules from the solutions bonded to the antigens immobilized on electrode 12. No antibody-antigen bonding was observed in solutions having a pH greater than or equal to 10.

At t=1040 seconds, the antibody solutions were replaced with otherwise identical solutions devoid of antibodies. As a result, as is seen from FIG. 6A, bonded affinity pairs on the surface of electrode 12 dissociated to release the antibody, the rate of release increasing with increased solution pH.

In a similar study, three succeeding 10-second long potential pulses (−0.6V, −0.9V and −1.1 V) were applied to electrode 12 in each of the four channels. As is seen in FIG. 6B, the rate of dissociation of the bonded affinity pairs increased with more negative (more reductive) potentials and with higher pH.

Figure 7:
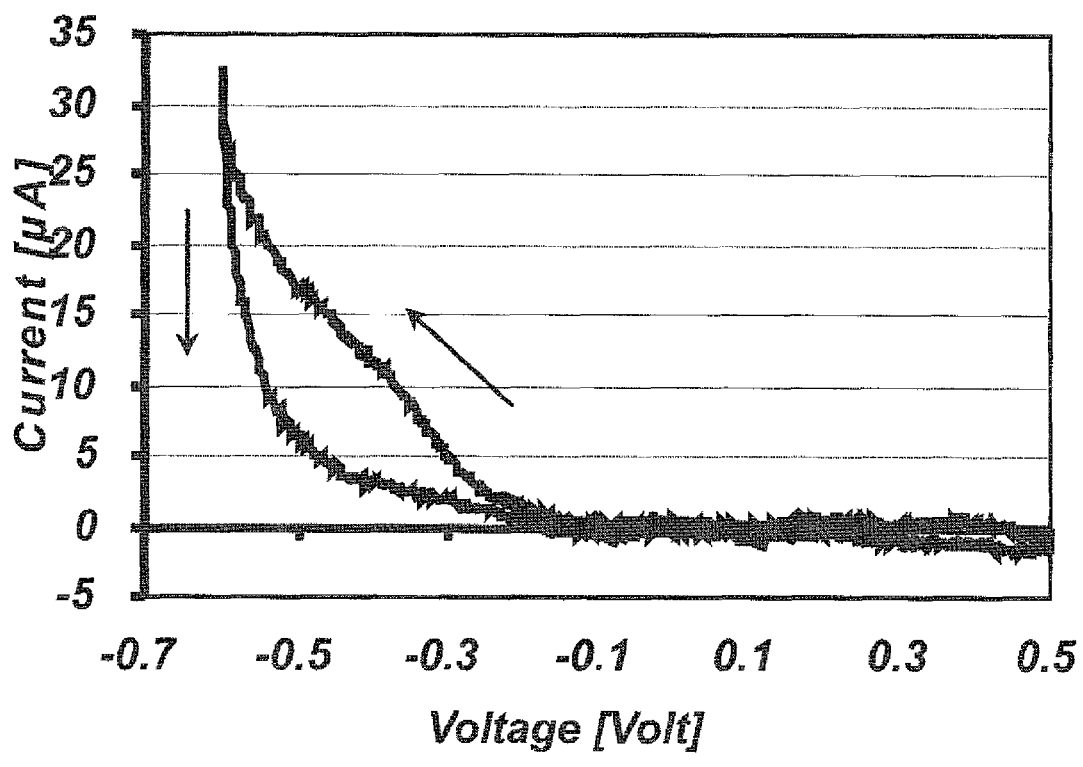
FIG. 7 shows the results of a cyclic voltammogram measured with an unpatterned SPR chip in a PBS solution (pH 7.2) relative to a KCl calomel reference electrode.

The attribution of the increased rate of dissociation of bonded affinity pairs to the increased concentration of hydroxyl anions resulting from the electrolysis of water is further substantiated by electrochemical measurements. FIG. 7 shows a cyclic volammogram (−0.6V to 0.5V to −0.6V, scan rate 50 mV/sec) measured in a PBS solution having a pH 7.2 with an unpatterned SPR chip (electrode area 0.69 cm$^2$). Potential was measured relative to a saturated calomel electrode, thus for direct comparison with FIG. 6B the bias in FIG. 7 must be offset by +45 mV, the calomel potential relative to the AgCl/Ag reference electrode 16 of electrode assembly 32. The shoulder at −0.4V in the negative going voltage scan is attributed to reduction of hydrated AuOH to gold and water. The sharp increase in current below −0.5V reflects the beginning of the hydrolysis of water to yield hydroxyl anions and H$_2$ molecules. The beginning of the hydrolysis of water coincides with the threshold for antibody/antigen dissociation seen in FIG. 6B.

Effect of Environmental Buffering Capacity

The attribution of the dissociation of bound affinity pairs to the effects of the concentration of electrolysis products is further substantiated by the influence of the buffering capacity of the solution.

Figure 8:
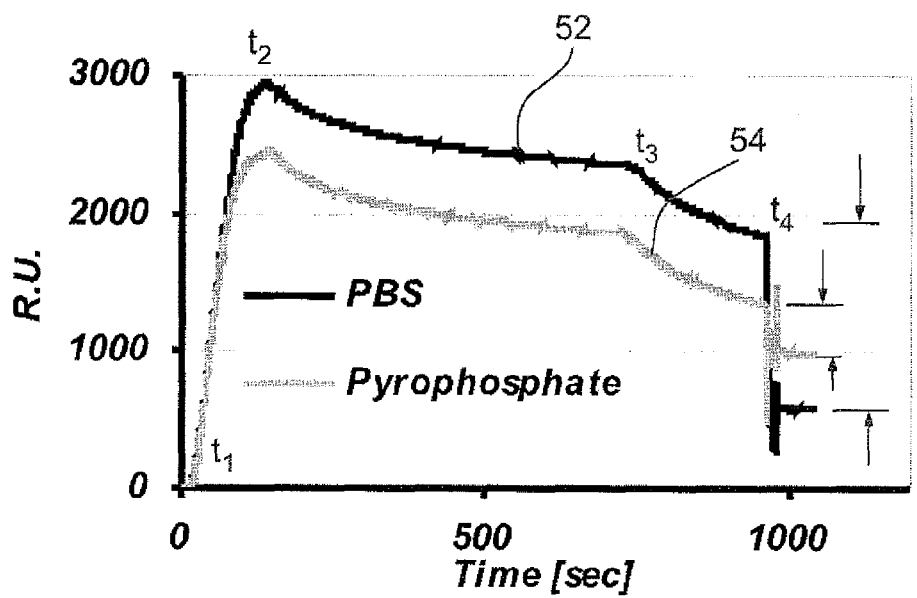
FIG. 8 shows experimental results demonstrating the effect of the buffering capacity of the environment on the controlled dissociation of an affinity pair of the present invention by comparing the dissociation of antibodies bound to immobilized antigens in a high buffering capacity buffer (pyrophosphate) and low buffering capacity buffer (PBS) both of pH 9.

Binding/controlled dissociation experiments were performed comparing solutions having the same pH but different buffering capacities. The results of such a comparison, of PBS and pyrophosphate buffers both having pH 9, are depicted in FIG. 8. PBS has a relatively low buffering capacity at pH 9 while pyrophosphate has a relatively high buffering capacity at pH 9.

At t1=30 seconds, an antibody PBS solution (pH 7.2) was passed through channels 40a and 40b of electrode assembly 32. As is seen in FIG. 8, antibody molecules bonded to the antigen molecules immobilized on electrode 12.

At t2=100 seconds, the antibody PBS solution passing through both channels 40a and 40b was replaced with a PBS solution (pH 7.2) devoid of antibody. As is seen in FIG. 8, the bonded affinity pairs slowly and gradually dissociated, releasing antibody molecules from electrode 12 to the solution.

At t3=750 seconds, a PBS solution (pH 9) was passed through channel 40a and a pyrophosphate solution (pH 9) was passed through channel 40h of electrode assembly 30. As is seen in FIG. 8, the bonded affinity pairs dissociated and the antibody molecules were released from electrode 12 at a rate faster than when the pH was 7.2, but was the same for both solutions having pH 9.

At t4=950 seconds, a potential difference of −0.9V was applied to electrode 12 for 15 seconds. As is seen in FIG. 8, the potential difference pulse led to the dissociation of approximately 3 times more affinity pairs with concomitant antibody release from the weakly buffering PBS than from the strongly buffering pyrophosphate.

Similar experiments performed using solutions having pH 9 having a high buffering capacity (Borate and Tris) or a low buffering capacity (Acetic acid) provided substantially similar results.

Similar experiments were performed using solutions having different buffer concentrations and the same ionic strength provided by sodium chloride. Affinity pair dissociation was maximal for pure NaCl and diminished monotonically with buffer concentration. The effect in the former case was similar in magnitude to that in PBS at pH 9.5.

CONCLUSIONS

As seen from the results above, the teachings of the present invention may be applied to control the affinity of a pair of chemical entities having a pH-dependent affinity and thus control the binding and dissociation of a pair of chemical entities in proximity of the surface of an electrode.

The experimental evidence indicates that under the conditions used electrolysis of water in the solution produces hydroxyl anions, which lowers the affinity of the antibody-antigen affinity pair to the extent that the associated affinity pair dissociated and the antibody released into the environment.

The experimental evidence supports a mechanism whereby hydroxyl anions are generated by electrolysis of water in close proximity of the surface of the electrode. Such hydroxyl anions presumably react with protons in the solution, lowering the concentration of protons in proximity of the electrode, raising the pH of the environment, causing the lowering of affinity of the affinity pair.

When the potential difference between the electrode and the reference electrode is nullified, antibodies bond with the immobilized antigen indicating that the electrolysis products are neutralized so that the affinity of the affinity pair returns to the original higher value. Presumably, this is a result of the pH of the environment proximate to the surface of the electrode returning to the original bulk value. This is supported by the experimental results in high and low buffering capacity environments.

Other Factors

Presumably, there are also other factors affecting the environment in proximity of the electrode surface when the potential is applied. In addition to electrolysis, the applied negative potential difference generates an electrostatic field that presumably attracts protons towards the electrode surface, an effect that would decrease the pH in proximity of the electrode surface. At lower applied negative potentials, this effect is amplified by chemisorption of chlorine anions to the gold surface of an electrode. Apparently, these factors do not significantly affect the teachings of the present invention as electrostatic effects and current manifest on two different scales. Whereas electrostatic effects decay on scales comparable to screening length ($\lambda \sim 1$ nm of 0.1 M NaCl) the effect of current is long range, leading to a slower decay of the hydroxyl concentration as a function of distance.

It is appreciated that certain features of the invention, which are, for clarity, described in the context of separate some embodiments, may also be provided in combination in a single embodiment. Conversely, various features of the invention, which are, for brevity, described in the context of a single embodiment, may also be provided separately or in any suitable subcombination.

Although the invention has been described in conjunction with specific some embodiments thereof, it is evident that many alternatives, modifications and variations will be apparent to those skilled in the art. Accordingly, it is intended to embrace all such alternatives, modifications and variations that fall within the spirit and broad scope of the appended claims, All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of changing the affinity of a pair of chemical entities having a pH-dependent affinity, wherein the pair of chemical entities constitutes an affinity pair being a pair of two molecules that are capable of mutually bind non-covalently with high specificity and dissociate, the method comprising:

a) immobilizing a first member of said pair of chemical entities having a pH-dependent affinity to a surface of an electrode;
 b) immersing said first member of said pair of chemical entities in an electrolysable environment so that said electrode is in electrical contact with said environment where a second member of said pair of chemical entities is found in said environment;
 c) making electrical contact between a counter electrode and said environment; and
 d) changing a potential between said electrode and said counter electrode so as to substantially change electrolysis of said environment thereby changing said affinity of said chemical entities so as to bind or dissociate reversibly by substantially changing a concentration of electrolysis products in said environment in proximity of said surface of said electrode.

2. The method of claim 1, wherein said electrolysis products are products of electrolysis of water.

3. The method of claim 1, wherein said change of concentration of said electrolysis products in said environment is substantial up to about 100 nanometer from said surface of said electrode.

4. The method of claim 1, further comprising:
   e) monitoring a pH of said environment in said proximity of said surface.

5. The method of claim 4, wherein said changing of said potential is with reference to said monitoring.

6. The method of claim 1, wherein said pair of chemical entities is an antibody-antigen affinity pair.

7. The method of claim 1, further comprising: immobilizing said second member of said pair of chemical entities to said surface of said electrode so that said first member and said second member of said pair of chemical entities are within binding distance.

8. The method of claim 7, wherein said pair of chemical entities is a DNA-histone affinity.

9. The method of claim 8, wherein said changing of said potential regulates transcription of said DNA.

10. The method of claim 9, further comprising providing RNA polymerase in said environment so as to allow said transcription of said DNA.

11. A method of changing the affinity of a pair of chemical entities having a pH-dependent affinity, comprising:
   a) immobilizing a first member of said pair to a surface of an electrode and immobilizing a second member of said pair to said surface so that said first member and said second member of said pair are within binding distance;
   b) immersing said first member and said second member of said pair in an electrolysable environment so that said electrode is in electrical contact with said environment;
   c) making electrical contact between a counter electrode and said environment; and
   d) changing a potential between said electrode and said counter electrode so as to substantially change electrolysis of said environment thereby changing said affinity of said first member and said second member reversibly by substantially changing a concentration of electrolysis products in said environment in proximity of said surface of said electrode.

12. The method of claim 11, wherein said pair of chemical entities is a DNA-histone affinity pair.

13. The method of claim 12, wherein said changing of said potential regulates transcription of said DNA.

14. The method of claim 13, further comprising providing RNA polymerase in said environment so as to allow said transcription of said DNA.

15. A method of changing the affinity of a DNA-histone affinity pair, comprising:
   a) immobilizing said DNA to a surface of an electrode and immobilizing said histone to said surface so that said DNA and said histone are within binding distance;
   b) immersing said DNA and said histone in an electrolysable environment so that said electrode is in electrical contact with said environment;
   c) making electrical contact between a counter electrode and said environment; and
   d) changing a potential between said electrode and said counter electrode so as to substantially change electrolysis of said environment thereby changing said affinity of said pair reversibly by substantially changing a concentration of electrolysis products in said environment in proximity of said surface of said electrode.

16. The method of claim 15, wherein said changing of said potential regulates transcription of said DNA.

17. The method of claim 16, further comprising providing RNA polymerase in said environment so as to allow said transcription of said DNA.

18. A method of changing the affinity of a pair of chemical entities having a pH-dependent affinity, wherein the chemical entities constitute an affinity pair having each member thereof selected from the group consisting of a peptide, a polypeptide and a protein, the method comprising:
   a) immobilizing a first member of said pair of chemical entities having a pH-dependent affinity to a surface of an electrode;
   b) immersing said first member of said pair of chemical entities in an electrolysable environment so that said electrode is in electrical contact with said environment where a second member of said pair of chemical entities is found in said environment;
   c) making electrical contact between a counter electrode and said environment; and
   d) changing a potential between said electrode and said counter electrode so as to substantially change electrolysis of said environment thereby changing said affinity of said chemical entities so as to bind or dissociate reversibly by substantially changing a concentration of electrolysis products in said environment in proximity of said surface of said electrode.

19. The method of claim 18, wherein said electrolysis products are products of electrolysis of water.

20. The method of claim 18, wherein said change of concentration of said electrolysis products in said environment is substantial up to about 100 nanometer from said surface of said electrode.

21. The method of claim 18, further comprising:
   e) monitoring a pH of said environment in said proximity of said surface.

22. The method of claim 21, wherein said changing of said potential is with reference to said monitoring.

23. The method of claim 18, wherein said pair of chemical entities is an antibody-antigen affinity pair.

24. The method of claim 18, further comprising: immobilizing said second member of said pair of chemical entities to said surface of said electrode so that said first member and said second member of said pair of chemical entities are within binding distance.

* * * * *